(12) United States Patent
Berry et al.

(10) Patent No.: US 10,099,043 B2
(45) Date of Patent: Oct. 16, 2018

(54) HOLLOW MICRONEEDLE ARRAY ARTICLE

(71) Applicant: 3M INNOVATIVE PROPERTIES COMPANY, St. Paul, MN (US)

(72) Inventors: Dennis G. Berry, Maplewood, MN (US); Paul A. Martinson, Maplewood, MN (US); Ryan Patrick Simmers, Fargo, ND (US)

(73) Assignee: 3M Innovative Properties Company, St. Paul, MN (US)

( * ) Notice: Subject to any disclaimer, the term of this patent is extended or adjusted under 35 U.S.C. 154(b) by 323 days.

(21) Appl. No.: 14/905,018

(22) PCT Filed: Jul. 10, 2014

(86) PCT No.: PCT/US2014/046111
§ 371 (c)(1),
(2) Date: Jan. 14, 2016

(87) PCT Pub. No.: WO2015/009530
PCT Pub. Date: Jan. 22, 2015

(65) Prior Publication Data
US 2016/0151617 A1   Jun. 2, 2016

Related U.S. Application Data

(60) Provisional application No. 61/846,905, filed on Jul. 16, 2013.

(51) Int. Cl.
*A61M 37/00* (2006.01)
*A61B 5/15* (2006.01)

(52) U.S. Cl.
CPC ... *A61M 37/0015* (2013.01); *A61B 5/150022* (2013.01); *A61B 5/150282* (2013.01);
(Continued)

(58) Field of Classification Search
CPC ...... A61M 37/0015; A61M 2037/0023; A61M 2037/003; A61M 2037/0061; A61B 5/150396
See application file for complete search history.

(56) References Cited

U.S. PATENT DOCUMENTS 3,308,822 A   3/1967   De Luca
4,490,139 A   12/1984  Huizenga et al.
(Continued)

FOREIGN PATENT DOCUMENTS

CN   101244303 B      9/2010
DE   10 2008 052 749  5/2010
(Continued)

*Primary Examiner* — Sean Dougherty
(74) *Attorney, Agent, or Firm* — Eric E. Silverman

(57) ABSTRACT

An article 100 having a first side 112 that has a central portion 130 defined by a first edge 134, a microneedle-free peripheral portion 140 that substantially surrounds the central portion, and a plurality of spaced-apart hollow microneedles 160. Each microneedle has a body that includes an outer surface 163; a base segment 166 having a base 162 and a first shape; a tip segment 168 having a tip 164 and a second shape, wherein the second shape is distinct from the first shape; a transition plane 167 that delineates the base segment and the tip segment; and a central axis 180. An angle, defined by an intersection of the central axis of at least one microneedle and a shortest line extending from the first edge and through the transition plane of the at least one microneedle, is less than about 50°.

19 Claims, 9 Drawing Sheets

(52) U.S. Cl.
CPC .. *A61B 5/150396* (2013.01); *A61B 5/150984* (2013.01); *A61M 2037/003* (2013.01); *A61M 2037/0023* (2013.01); *A61M 2037/0061* (2013.01)

(56) References Cited

U.S. PATENT DOCUMENTS

| | | |
|---|---|---|
| 5,575,780 A | 11/1996 | Saito |
| 5,752,942 A | 5/1998 | Doyle et al. |
| 6,091,975 A | 7/2000 | Daddona et al. |
| 6,312,612 B1 | 11/2001 | Sherman et al. |
| 6,379,324 B1 | 4/2002 | Gartstein et al. |
| 6,451,240 B1 | 9/2002 | Sherman et al. |
| 6,471,903 B2 | 10/2002 | Sherman et al. |
| 6,517,523 B1 | 2/2003 | Kaneko et al. |
| 6,558,361 B1 | 5/2003 | Yeshurun |
| 6,824,378 B2 | 11/2004 | King et al. |
| 7,070,583 B1 | 7/2006 | Higuchi et al. |
| 7,648,484 B2 | 1/2010 | Yeshurun et al. |
| 8,088,321 B2 | 1/2012 | Ferguson et al. |
| 8,246,893 B2 | 8/2012 | Ferguson et al. |
| 2005/0065463 A1 | 3/2005 | Tobinaga et al. |
| 2005/0261631 A1 | 11/2005 | Clarke et al. |
| 2006/0202385 A1 | 9/2006 | Xu et al. |
| 2009/0054842 A1 | 2/2009 | Yeshurun et al. |
| 2009/0099537 A1 | 4/2009 | DeVoe et al. |
| 2010/0193997 A1 | 8/2010 | Frederickson et al. |
| 2010/0305516 A1 | 12/2010 | Xu et al. |
| 2011/0046556 A1 | 2/2011 | Kraft |
| 2011/0172605 A1 | 7/2011 | Berenschot et al. |
| 2011/0172609 A1 | 7/2011 | Moga et al. |
| 2011/0192562 A1 | 8/2011 | Motoi et al. |
| 2011/0213335 A1 | 9/2011 | Burton et al. |
| 2012/0041337 A1 | 2/2012 | Ferguson et al. |
| 2012/0123387 A1 | 5/2012 | Gonzalez et al. |
| 2012/0258284 A1 | 10/2012 | Rendon |
| 2014/0236075 A1 | 8/2014 | Sugimura |

FOREIGN PATENT DOCUMENTS

| | | |
|---|---|---|
| EP | 2 062 611 | 5/2009 |
| WO | WO 2006/025786 | 3/2006 |
| WO | WO 2008/027011 | 3/2008 |
| WO | WO 2009/130926 | 10/2009 |
| WO | WO 2012/074576 | 6/2012 |
| WO | WO 2012/122162 | 9/2012 |
| WO | WO 2012/126784 | 9/2012 |
| WO | WO 2013/061825 | 5/2013 |
| WO | WO 2014/099404 | 6/2014 |
| WO | WO 2014/105458 | 7/2014 |
| WO | WO 2015/009523 | 1/2015 |
| WO | WO 2015/009524 | 1/2015 |
| WO | WO 2015/009531 | 1/2015 |

HOLLOW MICRONEEDLE ARRAY ARTICLE

CROSS REFERENCE TO RELATED APPLICATIONS

This application is a national stage filing under 35 U.S.C. 371 of PCT/US2014/046111, filed Jul. 10, 2014, which claims priority to U.S. Provisional Patent Application No. 61/846,905, filed Jul. 16, 2013, the disclosure of which is incorporated by reference in its entirety herein.

BACKGROUND

Transdermal and topical drug delivery can be used for therapeutic treatment, but the number of molecules that can be effectively delivered using these routes can be limited by the barrier properties of skin. The main barrier to transport of molecules through the skin is the stratum corneum (the outermost layer of the skin).

A number of different skin treatment methods have been proposed in order to increase the permeability or porosity of the outermost skin layers, such as the stratum corneum, thus enhancing drug delivery through or into those layers. The stratum corneum is a complex structure of compact keratinized cell remnants separated by lipid domains. The stratum corneum is formed of keratinocytes, which comprise the majority of epidermal cells that lose their nuclei and become corneocytes. These dead cells comprise the stratum corneum, which has a thickness of only about 10-30 microns and protects the body from invasion by exogenous substances and the outward migration of endogenous fluids and dissolved molecules. Various skin treatment methods include the use of microneedles, laser ablation, RF ablation, heat ablation, sonophoresis, iontophoresis, or a combination thereof.

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum such that the therapeutic agents and other substances can sequentially or simultaneously pass through that layer and into the tissues below. Microneedles of these devices pierce the stratum corneum upon contact, making a plurality of microscopic slits which serve as passageways through which molecules of active components can be delivered into the body. In delivering an active component, the microneedle device can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated on the microneedle array and delivered directly through the skin after the stratum corneum has been punctured.

Microneedle array articles can be used in conjunction with an applicator device capable of being used several times or as a single-use device. The microneedle array articles are generally used once and then discarded.

SUMMARY

The present inventors recognized that issues related to the use of hollow microneedles include the ability to effectively and consistently insert the needles to a desired depth in the skin, the ability to reliably hold the microneedles in proper contact with the skin during the period of administration, and the ability to apply consistent force for delivery of materials (e.g., pharmaceutically-active compounds) into the skin.

It has now been found that an interaction between an article comprising a plurality of hollow microneedles and a skin surface against which the article is urged can result in undesirable effects on the penetration of at least one microneedle of the plurality into the skin. It has further been found that, when the article comprises an array of microneedles, one of the effects can be significant variability in the depth of penetration into the skin by one or more of the microneedles in the array. The present inventors recognized the consistency of penetration depth can be controlled by including several features into the design of the article. The inventive design features result in the ability to effectively and consistently insert the needles to a desired depth in the skin. In addition, certain features of the inventive design permit simpler, more robust processes to be used for the manufacture of the articles.

The present disclosure generally relates to articles comprising microneedles and their use to deliver materials through the surface of skin or remove biological fluids through the surface of skin. In particular, the present disclosure relates to an article comprising an array of a plurality of microneedles that is configured to provide consistent depths of penetration for each microneedle of the plurality of microneedles by facilitating the contact between microneedles and skin and by reducing the possibility of contact between skin and non-microneedle surfaces during the use of the articles.

Some aspects of the present disclosure provide an article. The article can comprise a first side. The first side can comprise a central portion defined by a first edge, a microneedle-free peripheral portion that substantially surrounds the central portion, and a plurality of spaced-apart hollow microneedles extending from the central portion in a first direction. Each microneedle of the plurality comprises a body that includes an outer surface, a base segment having a base and a first shape that is defined by the outer surface, a tip segment having a tip and a second shape that is defined by the outer surface wherein the second shape is distinct from the first shape, a transition plane that delineates the base segment and the tip segment, a hollow channel extending through the body of the microneedle from a first opening proximate the tip to a second opening proximate the base, and a central axis. The plurality of hollow microneedles can form an array that comprises three or more perimeter microneedles disposed proximate the first edge. The central portion is not coplanar with the peripheral portion. The peripheral portion can be canted in a second direction relative to the central portion, wherein the second direction is opposite the first direction. An angle, defined by an intersection of the central axis of at least one of the plurality of microneedles and a shortest line extending from the first edge and through the transition plane of the at least one microneedle, can be less than about 50°.

Other aspects of the present disclosure provide an article. The article can comprise a first side. The first side can comprise a central portion defined by a first edge, a microneedle-free peripheral portion that substantially surrounds the central portion, and a plurality of spaced-apart hollow microneedles extending from the central portion in a first direction. Each microneedle of the plurality comprises a body that includes an outer surface, a base segment having a base and a first shape that is defined by the outer surface, a tip segment having a tip and a second shape that is defined by the outer surface wherein the second shape is distinct from the first shape, a transition plane that delineates the base segment and the tip segment, a hollow channel extending through the body of the microneedle from a first opening proximate the tip to a second opening proximate the base, and a central axis. The plurality of hollow microneedles can form an array that comprises three or more perimeter microneedles disposed proximate the first edge. The central portion is not coplanar with the peripheral portion. The peripheral portion can be canted in a second direction relative to the central portion, wherein the second direction is opposite the first direction. Each of the three or more perimeter microneedles comprises a height measured from the base to the tip. The tip segment of each of the three or more perimeter microneedles can define at least about 30% of the height of the at least one microneedle.

Other aspects of the present disclosure provide the use of any embodiment of the above hollow microneedle article for injecting fluid into a body. Other aspects of the present disclosure provide the use of any embodiment of the above hollow microneedle article for extracting fluid from a body.

The phrase "injection apparatus" refers to an integrated device capable of delivering or extracting a fluid over a certain period and is not limited to devices intended solely for an infusion. Accordingly, an injection apparatus may be used, for example, for injecting fluid into the dermis or extracting fluid from tissue.

The term "transdermally" and variations thereof, is generally used to refer to any type of delivery of an active ingredient that crosses any portion of skin. That is, transdermally can generally include systemic delivery (i.e., where the active ingredient is transported across, or substantially through, the dermis such that the active ingredient is delivered into the bloodstream), as well as intradermal delivery (i.e., where the active ingredient is transported partially through the dermis, e.g., across the outer layer (stratum corneum) of the skin, where the active ingredient is delivered into the skin, e.g., for treating psoriasis or for local anesthetic delivery). That is, transdermal delivery as used herein includes delivery of an active ingredient that is transported across at least a portion of skin (but not necessarily all of the layers of skin), rather than merely being topically applied to an outer layer of the skin.

The phrase "hollow microneedle" refers to a specific microscopic structure that is designed for piercing the stratum corneum to facilitate the delivery of drugs through the skin. By way of example, microneedles can include needle or needle-like structures, as well as other structures capable of piercing the stratum corneum and delivering liquid drug formulations to skin or tissue layers beneath the stratum corneum.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

As used herein, "a," "an," "the," "at least one," and "one or more" are used interchangeably. Thus, for example, a microneedle can be interpreted to mean "one or more" microneedles.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Additional details of these and other embodiments are set forth in the accompanying drawings and the description below. Other features, objects and advantages will become apparent from the description and drawings, and from the claims.

BRIEF DESCRIPTION OF DRAWINGS

The present invention will be further explained with reference to the drawing figures listed below, where like structure is referenced by like numerals throughout the several views.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to articles comprising microneedles and their use to deliver materials (e.g., pharmaceutically-active compounds) through the surface of skin or remove biological fluids through the surface of skin. In particular, the present disclosure relates to an article comprising an array of a plurality of hollow microneedles that is configured to provide consistent depths of penetration for each microneedle of the plurality of hollow microneedles by facilitating the contact between microneedles and skin and by reducing the possibility of contact between skin and non-microneedle surfaces during the use of the articles.

Figure 1:
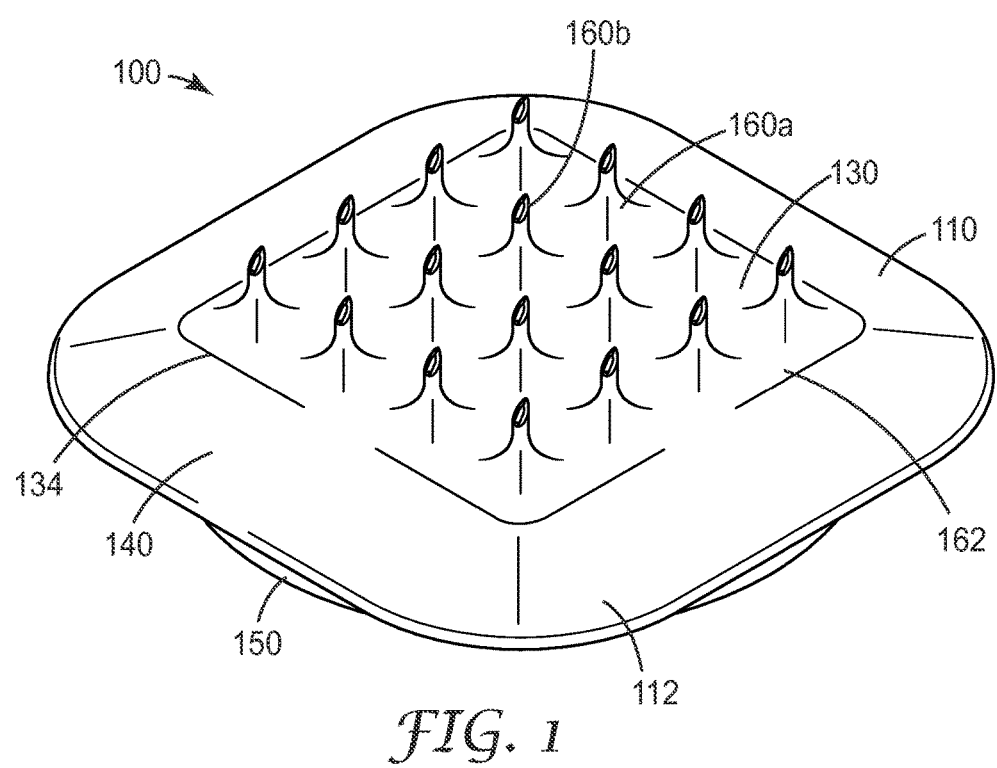
FIG. 1 is a perspective view of a first side of one embodiment of an article comprising an array of hollow microneedles according to the present disclosure.

Turning to the drawings, FIGS. 1-5 show various views of one embodiment of an article 100 according to the present disclosure. The article 100 comprises a first side 112 and a second side 114. In any embodiment, the second side 114 can be opposite the first side 112. The first side 112 comprises central portion 130 with a plurality of spaced-apart hollow microneedles 160 extending therefrom in a first direction designated by arrow "A" (see FIG. 3). The spaced-apart microneedles 160 form an array. In any embodiment, the array of microneedles optionally may be square-shaped, as shown in FIG. 1.

Figure 2:
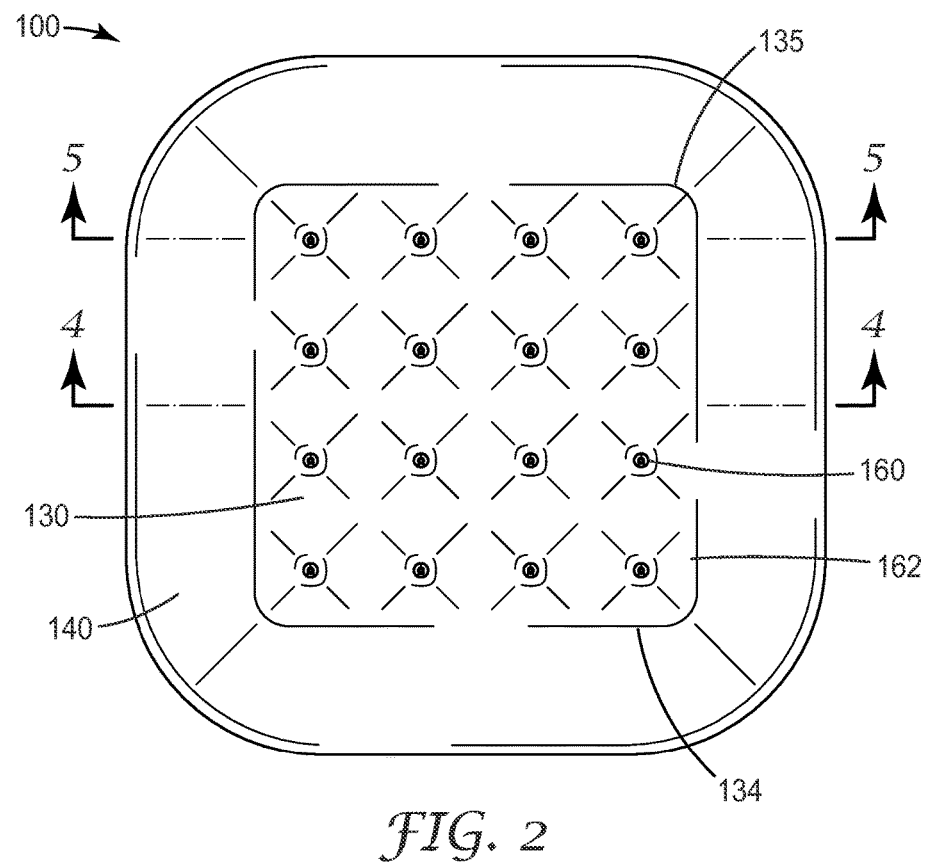
FIG. 2 is a plan view of the first side of the article of FIG. 1.

An outer boundary of the central portion 130 is defined by a first edge 134 that surrounds the microneedles 160. Disposed in the central portion 130 proximate the first edge 134 are three or more perimeter microneedles 160a. The perimeter microneedles 160a are the outermost microneedles (i.e., the microneedles closest to the first edge, which defines the outer boundary of the central portion 130. Optionally, the first edge 134 may form a radius of curvature 135 (e.g., at a corner, as shown in FIG. 2). In any embodiment, the perimeter microneedles are approximately equally-spaced apart from the first edge 134. In any embodiment, the perimeter microneedles define a two-dimensional first geometric shape (e.g., a polygonal shape such as a triangle square, a rectangle, a hexagon). The first geometric shape defines a first area. Optionally, the array of microneedles further comprises one or more interior microneedles 160b disposed within the first area defined by the perimeter microneedles 160a.

Figure 3:
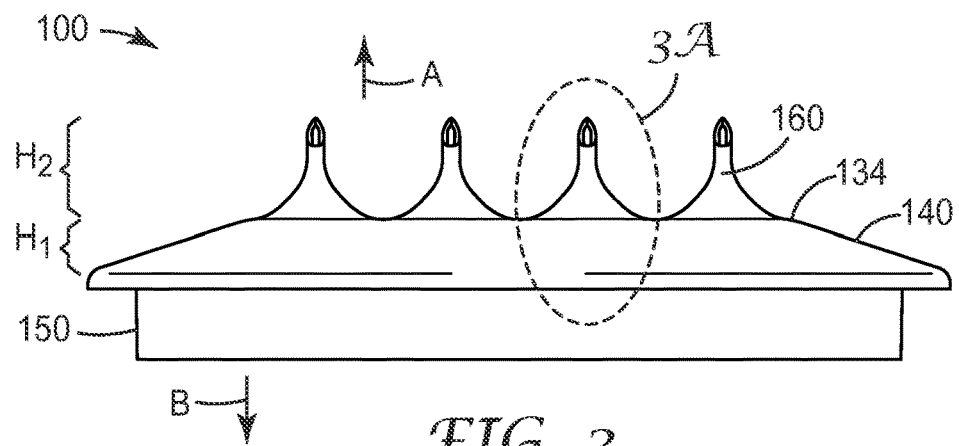
FIG. 3 is a side view of the article of FIG. 1.
Figure 3A:
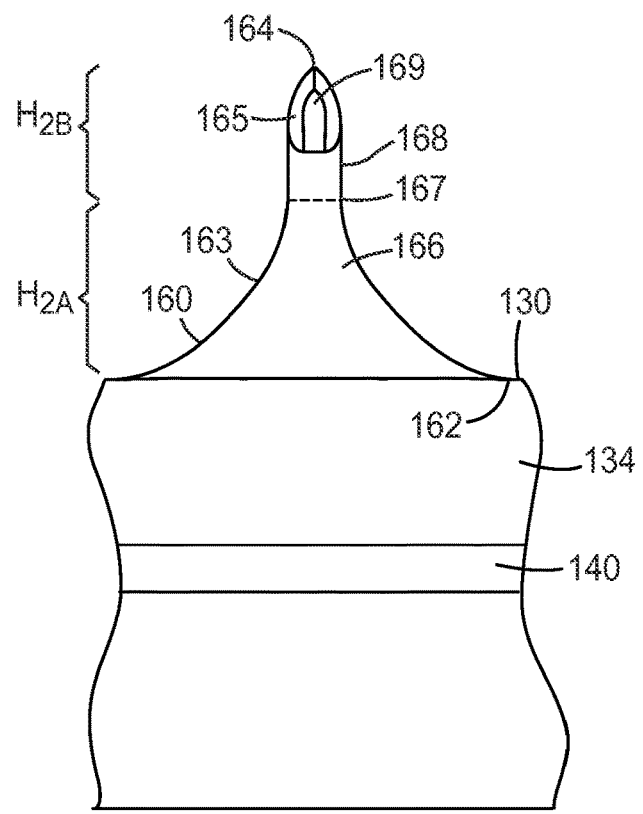
FIG. 3A is a detail view of one of the hollow microneedles of FIG. 3.

FIG. 3A shows a detail view of one of the hollow microneedles 160 of the article 100 of FIG. 3. In any embodiment of the article 100, each microneedle 160 of the plurality comprises a body that comprises an outer surface 163, a base segment 166, and a tip segment 168. The base segment 166 comprises a base 162 where the microneedle 160 extends from the central portion 130. The base segment 166 has a first shape that is defined by the outer surface 163 of the base segment. In the illustrated embodiment of FIG. 3A, the first shape is crateriform (i.e., a generally-conical shape with a radius of curvature) and, thus, is wider proximate that base 162. In contrast, the second shape defined by the outer surface 163 of the tip segment 168, excluding the bevel 165, is substantially cylindrical. In any embodiment, a substantially-cylindrical second shape may include a declination (i.e., deviation from normal) up to 10°, thereby making the tip segment 168 slightly narrower proximate the tip 164.

The tip segment 168 comprises a tip 164. The tip 164 is the part of the microneedle 160 that is furthest away from the base 162. The tip segment 168 has a second shape that is defined by the outer surface 163 of the microneedle 160. The second shape is distinguishable from the first shape. The respective shapes of the base segment 166 and the tip segment 168 become distinguishable at a transition plane 167. "Transition plane", as used herein is the plane where an angle formed by a tangent of the outer surface 163 of the microneedle and the central axis changes from a first (tip-proximal) angle of ≤10° to a second (tip-distal) angle of greater than about 10°. In the illustrated embodiment of FIG. 3A, the outer surface 163 of the microneedle 160 is substantially parallel to the central axis (not shown). However, at the transition plane 167, the substantially straight outer surface of the tip segment 168 (i.e. second shape) changes to a flared radius of curvature of the base segment 166 (i.e. first shape) and the angle formed by the intersection of a tangent (not shown) of the outer surface and the central axis (not shown) becomes greater than about 10°. The substantially cylindrically-shaped tip segment 168 of FIG. 2A is truncated by a bevel 165 that forms a tip 164 that is sharp enough to pierce stratum corneum.

Figure 4:
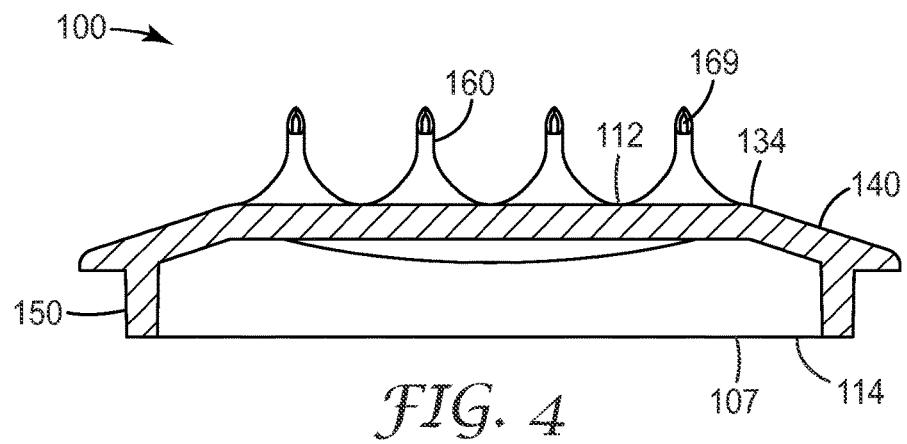
FIG. 4 is a cross-sectional side view, along line 4-4, of the article of FIG. 2.
Figure 4A:
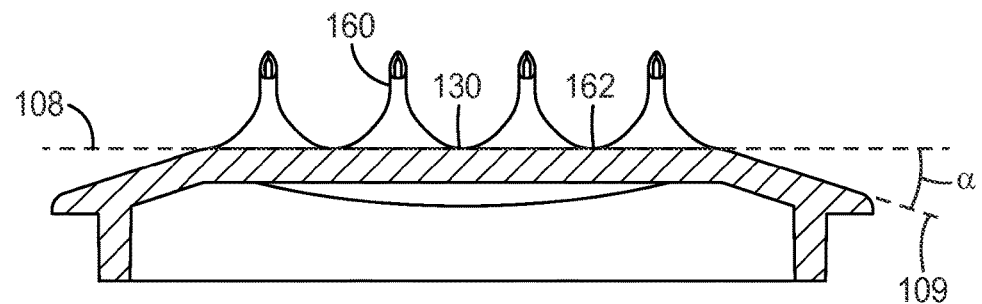
FIG. 4A is a duplicate of the view of FIG. 4, showing a first plane defined by the central portion and a second plane defined by the peripheral portion.

The microneedles 160 project away from the central portion 130 that is defined by the first edge 134. In any embodiment, the central portion 130 defines a planar surface (e.g., a substantially flat planar surface) from which the microneedles 160 project. FIG. 4A shows the substantially flat plane 108 formed by the central portion 130 and the bases 162 of the microneedles 160. In any embodiment, the central portion may define a curvilinear plane (not shown) that generally curves in a second direction (shown as arrow "B" in FIG. 3) that is opposite the first direction.

The first edge 134 is delineated by a change of the slope or radius of curvature of the first surface of the central portion 130. At the first edge 134, the slope of the first surface 112 changes in a direction toward the second direction B (i.e., away from the direction in which the microneedles 160 extend).

The first side 112 further comprises a microneedle-free peripheral portion 140 extending laterally from at least a part of the first edge 134 of the central portion 130. In any embodiment, the peripheral portion 140 substantially surrounds the central portion 130. The peripheral portion 140 is canted away from the central portion 130 in the second direction. The peripheral portion 140 defines a second plane 109 that is not coplanar with the plane 108 that is defined by the central portion 130, as shown in FIG. 4A. Thus, because the peripheral portion 140 is canted away from the central portion 130 of the article 100, the central portion 130 and the plurality of microneedles 160 extending therefrom project (in the first direction) away from the peripheral portion 140.

The angle α (shown in FIG. 4A) defines the extent to which the peripheral portion 140 is canted relative to the central portion. In any embodiment, the peripheral portion 140 can be canted at least about 10° to about 80 degrees. In any embodiment, the peripheral portion 140 can be canted at least about 15° to about 50 degrees. In any embodiment, the peripheral portion 140 can be canted at least about 18° to about 50 degrees. The canted surface of the peripheral portion 140 functions to absorb some of the force when the article 100 is urged against a skin surface (e.g., using an applicator as described below) without substantially interfering with the penetration of the microneedles.

In the illustrated embodiment of FIGS. 1-5, the central portion 130 and the peripheral portion 140 are formed as portions of a unitary body 110. However, in any embodiment, it is contemplated that the peripheral portion 140 and central portion 130 may be separate parts (not shown) that are disposed adjacent each other in the article.

Figure 5:
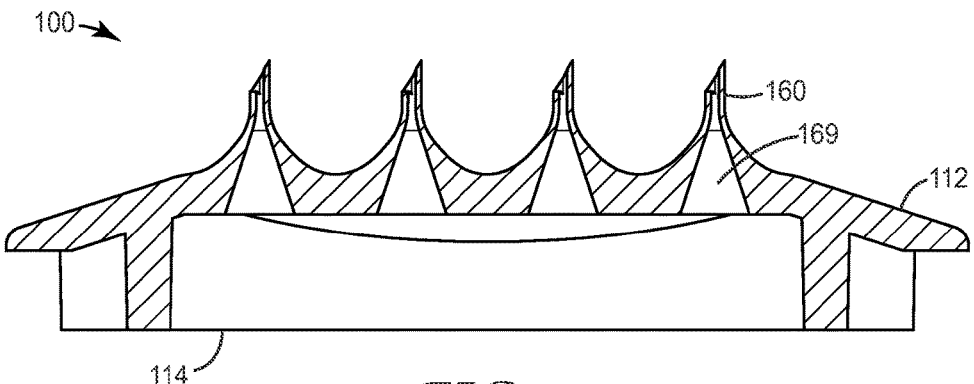
FIG. 5 is a cross-sectional side view, along line 5-5, of the article of FIG. 2.

In any embodiment, each of the plurality of microneedles 160 comprises a hollow channel 169. The hollow channel 169 optionally extends all the way through the article from the first surface 112 through the second surface 114, as shown in FIG. 5. In any embodiment, the hollow channel can provide a dead-end reservoir (e.g., a dead-end reservoir in the body of the microneedle, not shown) in which to load an active ingredient for injection/delivery into the skin, for example. In any embodiment, a hollow channel 169 extending through the article 100 can be fluidically connected to a reservoir 108 disposed on the second side of the article and an active ingredient can be infused into a patient from the reservoir 108 of the article 100 and through the hollow channel 169 of the microneedle 160.

Optionally, the article 100 further comprises a sidewall 150 extending substantially in the direction (i.e., second direction "B" shown in FIG. 3) opposite the plurality of microneedles 160. The side wall 150 of the illustrated embodiment forms a reservoir 108 on the second side 114 of the article 100. The reservoir 108 optionally can be sealed (not shown) and can contain an active agent (e.g., a drug) to be delivered by injection via plurality of hollow microneedles 160.

Referring to FIG. 3, the article can comprise at least two height dimensions. The first height dimension $H_1$ is the height of the canted peripheral portion 140 extending in the second direction B from the platform 130. The second height dimension $H_2$ is the height of the plurality of hollow microneedles 160 extending from the platform 130. Referring back to FIG. 3A, each microneedle 160 of the plurality comprises two height components (first height component $H_{2A}$ and second height component $H_{2B}$, respectively) that contribute to the total height of the microneedle 160. The first height component represents the height of the base segment 166 of the microneedle 160 and the second height component represents the height of the tip segment 168 of the microneedle. In any embodiment, the second height component of each microneedle of the plurality according to the present disclosure is about 300 μm to about 1000 μm. In any embodiment, the second height component of each microneedle of the plurality according to the present disclosure is about 650 μm to about 800 μm. In order to get consistent and effective delivery of an active compound to the proper location in the skin, the inventors have found that the configuration of an article comprising a plurality of microneedles according to the present disclosure should facilitate penetration of every microneedle of the plurality until at least the tip segment of each microneedle of the plurality is fully inserted into the skin.

In one aspect, in any embodiment, there may exist a predefined proportional relationship between first height component and the second height component of the at least one microneedle in an article according to the present disclosure. In any embodiment, the tip segment (as measured from the transition plane to the tip of at least one microneedle of the plurality of microneedles) defines at least about 30% of the height of the at least one microneedle. In any embodiment, the tip segment (as measured from the transition plane to the tip of each microneedle of the plurality of microneedles) defines at least about 30% of the height of the microneedles. In any embodiment, the tip segment (as measured from the transition plane to the tip of at least one microneedle of the plurality of microneedles) defines at least about 40% of the height of the at least one microneedle. In any embodiment, the tip segment (as measured from the transition plane to the tip of each microneedle of the plurality of microneedles) defines at least about 40% of the height of the microneedles. In any embodiment, the tip segment (as measured from the transition plane to the tip of at least one microneedle of the plurality of microneedles) defines at least about 50% of the height of the at least one microneedle. In any embodiment, the tip segment (as measured from the transition plane to the tip of each microneedle of the plurality of microneedles) defines at least about 50% of the height of the microneedles. In any embodiment, the tip segment (as measured from the transition plane to the tip of at least one microneedle of the plurality of microneedles) defines up to about 70% (inclusive) of the height of the at least one microneedle. In any embodiment, the tip segment (as measured from the transition plane to the tip of each microneedle of the plurality of microneedles) defines up to about 70% (inclusive) of the height of the microneedles.

Figure 6:
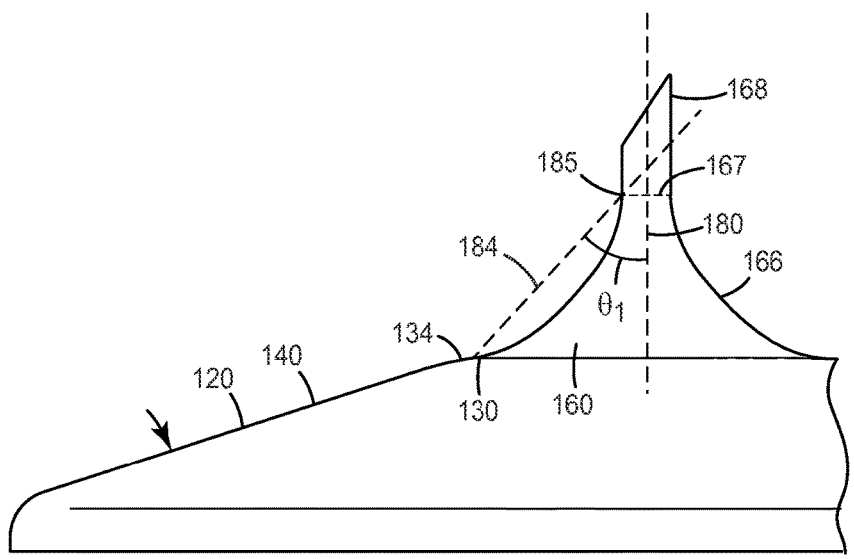
FIG. 6 is a detail side view of a portion of the article of claim 1, showing a spatial relationship between a perimeter microneedle and the central portion.

In any embodiment, each microneedle 160 of the plurality of microneedles of an article of the present disclosure comprises a central axis 180 as shown in FIG. 6. The central axis 180 also represents a longitudinal axis of the microneedle 160 extending through the microneedle from the base 162 toward the tip 164.

In one aspect, in any embodiment, there may exist a spatial relationship between at least one microneedle of the plurality of hollow microneedles and the first edge 134 of the central portion 130 from which the microneedle projects in an article according to the present disclosure. FIG. 6 shows a schematic view of a section of an article comprising at least one perimeter microneedle 160 according to the present disclosure. The article comprises a first side 112 having a central portion 130, a canted peripheral portion 140, and a first edge 134 disposed between the central portion 130 and the peripheral portion 140, as described above. Extending from the central portion 130 is one of a plurality of perimeter hollow microneedles 160a. The microneedle 160a comprises a base segment 166 with a first shape and a tip segment 168 with a second shape, the segments being separated by a transition line 167. Also shown in FIG. 6 is the central axis 180 of the microneedle 160 and a shortest line 184 extending from the first edge 134, through the closest point 185 of the transition plane 187 to the first edge 134, to the central axis 180. The intersection of the shortest line 184 with the central axis 180 forms an angle $\theta_1$. In any embodiment of the article of the present disclosure the angle $\theta_1$ is less than about 50°. In any embodiment, the angle $\theta_1$ is less than about 45°. In any embodiment, the angle $\theta_1$ is less than about 40°. In any embodiment, the angle $\theta_1$ is less than about 35°. In any embodiment, the angle $\theta_1$ is less than about 30°. In any embodiment, the angle $\theta_1$ is less than about 25°. In any embodiment, the angle $\theta_1$ is at least about 10°.

A person having ordinary skill in the art will appreciate that, as the angle $\theta_1$ decreases, the amount of potential area of central portion between the microneedle and the first edge also decreases. The significance of this relationship is discussed below. The spatial relationship discussed above may apply regardless of the first and second shapes defined by the base segment and the tip segment of the perimeter microneedles.

In any embodiment of an article according to the present disclosure, the transition plane of at least one microneedle of the plurality of hollow microneedles is disposed about 500 µm to about 1000 µm away from the central portion when measured along the central axis. In any embodiment of an article according to the present disclosure, the transition plane of at least one microneedle of the plurality of hollow microneedles is disposed about 500 µm to about 800 µm away from the central portion when measured along the central axis.

In any embodiment of an article according to the present disclosure, the height (measured from the base to the tip) of at least one microneedle of the plurality of hollow microneedles is about 600 µm to about 2000 µm. In any embodiment of an article according to the present disclosure, the height (measured from the base to the tip) of at least one microneedle of the plurality of hollow microneedles is about 800 µm to about 1800 µm. In any embodiment of an article according to the present disclosure, the height (measured from the base to the tip) of the at least one microneedle of the plurality of hollow microneedles is about 1200 µm to about 1600 µm. In any embodiment, all of the hollow microneedles of the plurality have approximately the same height (measured from the base to the tip).

Thus, in any embodiment, one or more of the plurality of hollow microneedles can have a first height component of 300-1000 µm and a second height component of 300-1000 Jim. In any embodiment, one or more of the plurality of hollow microneedles can have a first height component of 500-825 µm and a second height component of 500-825 µm. In any embodiment, one or more of the plurality of hollow microneedles can have a first height component of 500-825 µm and a second height component of 300-1000 µm. In any embodiment, one or more of the plurality of hollow microneedles can have a first height component of 300-1000 µm and a second height component of 500-825 µm.

Arrays of microneedles according to the present disclosure comprise a plurality of spaced-apart hollow microneedles extending from a plane (i.e., the central portion 130, as shown in FIGS. 1-5). FIGS. 7A-7D show the interaction of microneedles, skin, and the surface of the article from which the microneedle extends as the article is contacted with skin. These interactions illustrate at least one advancement (i.e., consistent penetration of microneedles, including perimeter microneedles) that the articles of the present disclosure provide over other configurations.

FIG. 7A-D show schematic views of a portion of an article 100 comprising at least one peripheral microneedle 160a as the article is urged against the surface 202 of skin. The article comprises a unitary body 112 comprising a first side 112 that comprises a central portion 130 with a hollow microneedle 160a extending therefrom and a peripheral portion 140 according to the present disclosure. The central portion 130 is defined by a first edge 134. The peripheral microneedle 160a comprises a base segment 166, a tip segment 168 with a tip 164, and a transition plane 167 disposed between the base segment and the tip segment.

Figure 7A:
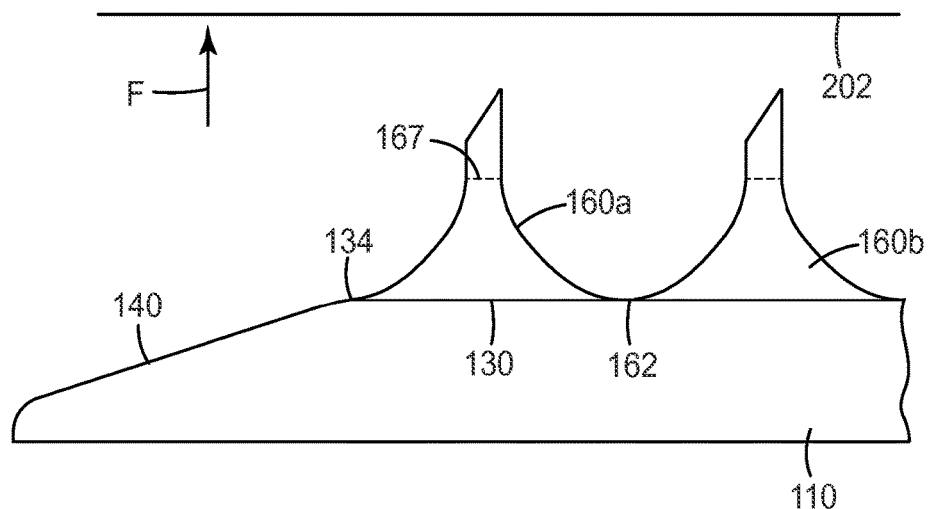
FIGS. 7A-D show a progression of schematic cross-sectional side views of two microneedles of an article according to the present disclosure as the microneedles penetrate a skin surface.
Figure 7B:
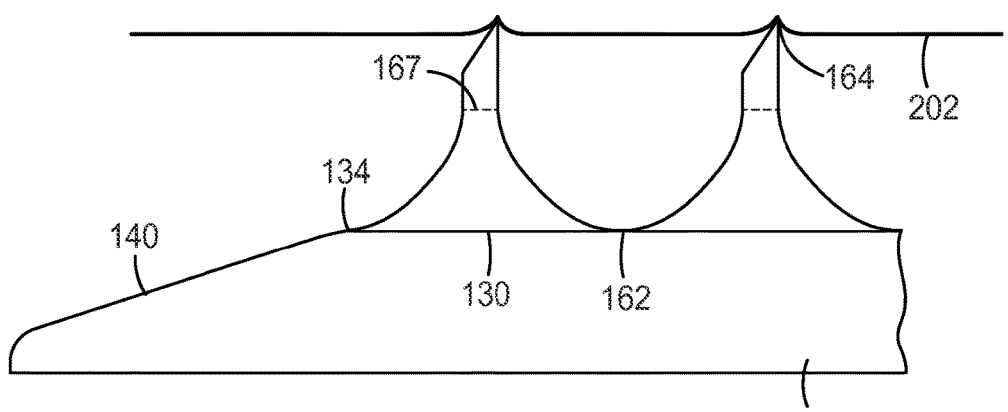
Figure 7C:
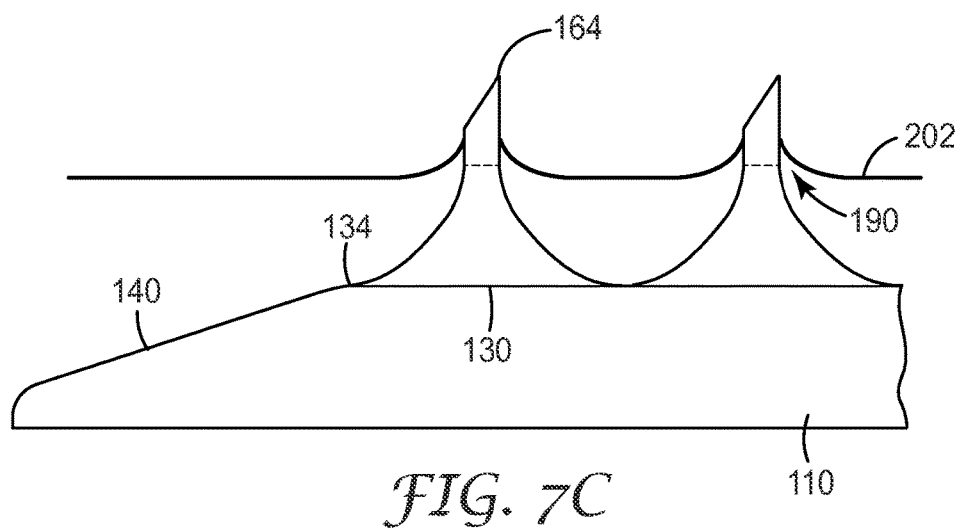
Figure 7D:
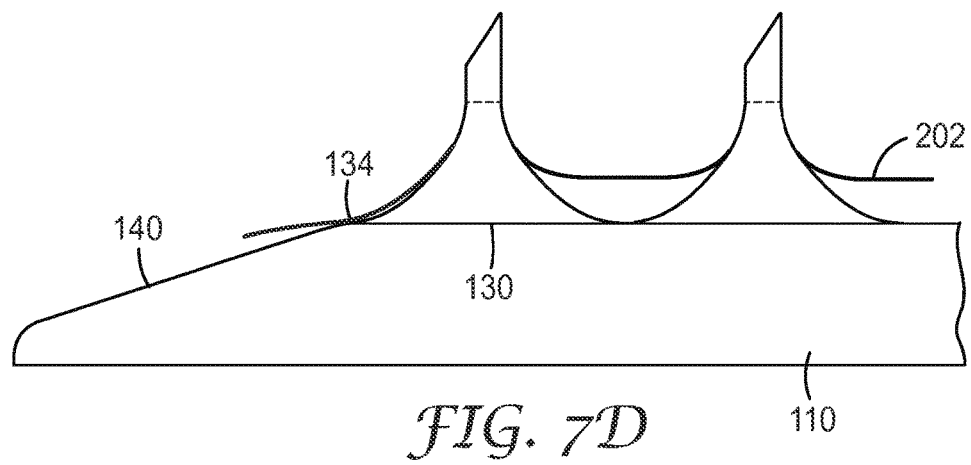

FIG. 7B shows the article 100 contacting the surface 202 of the skin. As the article is urged in the direction of arrow F, the tip 164 of the microneedle 160a begins to pierce the surface 202 of the skin. As the article 100 is urged further against the surface 202 of the skin, as shown in FIG. 7C, the tip 164 of the microneedle 160a passes through the surface 202 of the skin into the deeper layers of the skin (not shown). The resistance of the tissue to the penetration of the microneedle 160a causes "tenting" 190 of the skin surface 202 proximate the microneedle 160a. As more force is applied to the article 100, the tenting 190 becomes more pronounced, as shown in FIG. 7D. However, because of the dimensions of the peripheral microneedle 160a with respect to the central portion 130 and the peripheral portion 140 and because of the non-coplanar spatial relationships between the central portion 130 and the peripheral portion 140, the tented skin surface 202 does not contact the first side 112 of the article 100 in a manner that substantially interferes with the penetration of the microneedle 160a into the skin.

Although the distance between the perimeter microneedle 160a and the interior microneedle 160b is larger than the distance between the perimeter microneedle 160a and the first edge 134 of FIG. 7A-D, the skin surface 202 is prevented from contacting the central portion 130 adjacent the perimeter microneedle (e.g., perimeter microneedle 160a) because of contact between the skin surface 202 and the nearest-neighbor microneedle (e.g., microneedle 160b) in the array of microneedles. Thus, along the longitudinal dimension of the perimeter microneedles, consistent penetration depth of the microneedle tips is achieved.

Figure 8:
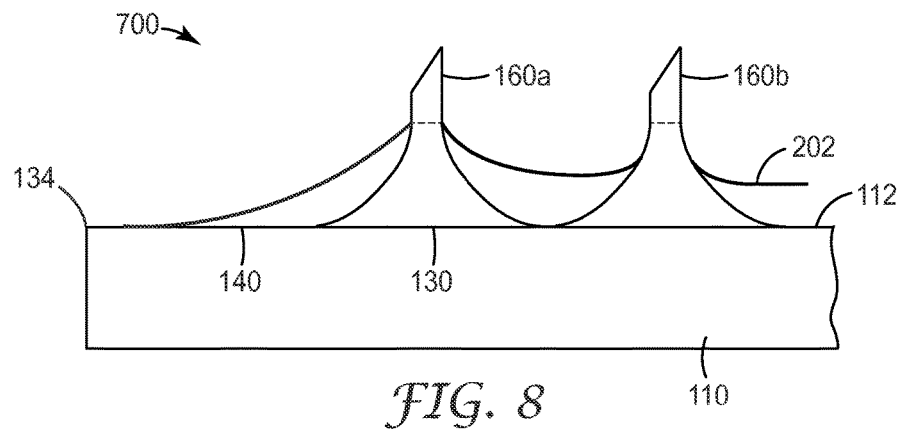
FIG. 8 is a schematic side view of an example of an article having a perimeter microneedle and an interior microneedle as the microneedles penetrate a skin surface.

FIG. 8 shows a schematic view of a portion of an article 700 comprising at least one peripheral microneedle 160a as the article is urged against the surface 202 of skin. The article of this comparative embodiment comprises a unitary body 110 comprising a first side 112 that comprises a central portion 130 with a perimeter hollow microneedle 160a and interior microneedle 160b extending therefrom. In addition, the article 100' includes a peripheral portion 140 that is not canted relative to the central portion. The central portion 130 is defined by a first edge 134. In contrast to the article 100 of FIGS. 7A-D, the first edge 134 is located further away from the perimeter microneedle 160a. The microneedles (microneedles 160a and 160b) of article 100' have the same general size and shape as the microneedles of the article 100 shown in FIGS. 7A-D. It is evident that the skin tenting 190 that occurs as the tip 164 penetrates the skin surface 202 causes the skin surface 202 to contact the first side 112. In the illustrated comparative embodiment of FIG. 8, this contact hinders penetration of the perimeter microneedle 160a to a preferred depth.

Without being bound by theory, it is believed that the contact between the skin surface 202 and the central portion 130 or the perimeter portion 140 can absorb a portion of the force that is otherwise used to urge the skin and the microneedles together, thereby lessening the amount of force available to facilitate deeper penetration of the microneedle tip 164. Although this contact may not obviate the ability of the microneedle to deliver an active ingredient, for example, through the skin; it may result in less consistency of the delivery of the active ingredient by one or more hollow microneedles (e.g., the perimeter microneedles) in an article comprising an array of hollow microneedles.

Figure 9:
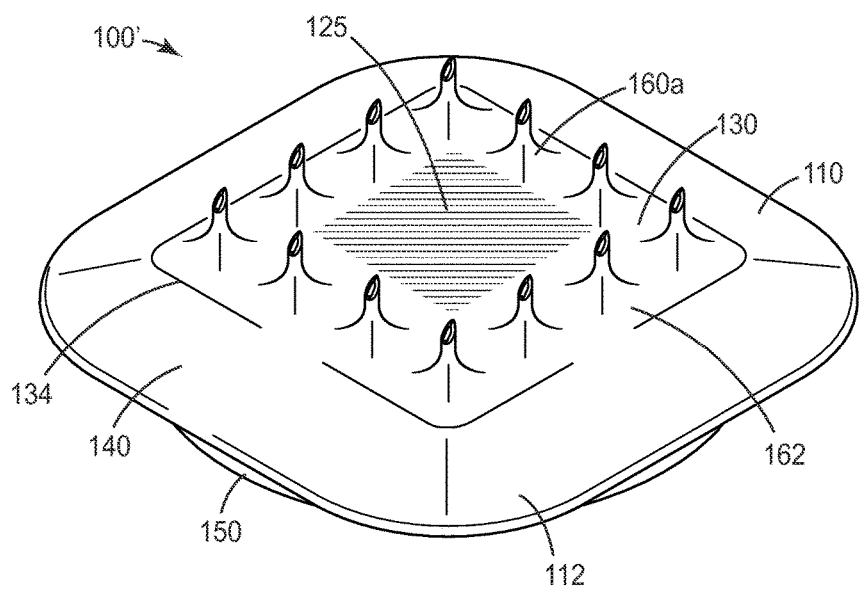
FIG. 9 is a perspective view of a first side of another embodiment of an article comprising an array of hollow microneedles according to the present disclosure.

In another aspect, the present disclosure provides an article comprising a plurality of microneedles that form an array, wherein the array comprises a first area comprising a plurality of perimeter microneedles and a microneedle-free second area 125 surrounded by the first area. FIG. 9 shows one embodiment of an article 100' comprising the microneedle-free-second area 125 according to the present disclosure. The article 100' comprises a central portion 130 having a plurality of perimeter microneedles 160a as discussed above. A first edge 134 defines the central portion 130. The article 100' further comprises a peripheral portion 140, which is not coplanar with the central portion 130, proximate the first edge 134. The peripheral portion 140 is canted with respect to the central portion 130 as described above. The central portion 130 further comprises a microneedle-free central area 125 (shaded area in FIG. 9).

The unshaded part of the central portion 130, which includes the area defined by the bases of the perimeter microneedles 160a, defines a perimeter area of the central portion 130. In any embodiment, the microneedle-free central area can be at least about 15% to about 99% (inclusive) of the total area (perimeter area plus central area) of the central portion 130. In any embodiment, the microneedle-free central area can about 20% to about 90% (inclusive) of the total area (perimeter area plus central area) of the central portion 130. In any embodiment, the microneedle-free central area can be about 30% to about 80% (inclusive) of the total area (perimeter area plus central area) of the central portion 130.

Microneedle articles (e.g., including articles comprising hollow microneedles) that are made according to the present disclosure can have a variety of configurations and features, such as those described in the following patents and patent applications, the disclosures of which are incorporated herein by reference in their entirety. One embodiment for microneedle array articles includes the structures disclosed in U.S. Patent Application Publication No. 2005/0261631 (Clarke et al.), which describes microneedles having a truncated tapered shape and a controlled aspect ratio. Another embodiment for the microneedle articles includes the structures disclosed in U.S. Pat. No. 6,091,975 (Daddona et al.), which describes blade-like microprotrusions for piercing the skin. Still another embodiment for the microneedle articles includes the structures disclosed in U.S. Pat. No. 6,312,612 (Sherman et al.), which describes tapered structures having a hollow central channel. Yet still another embodiment for the microneedle array articles includes the structures disclosed in U.S. Pat. No. 6,379,324 (Gartstein et al.), which describes hollow microneedles having at least one longitudinal blade at the top surface of the tip of the microneedle. A further embodiment for the microneedle array articles includes the structures disclosed in U.S. Patent Application Publication Nos. US2012/0123387 (Gonzalez et al.) and US2011/0213335 (Burton et al.), which both describe hollow microneedles. A still further embodiment for the microneedle array articles includes the structures disclosed in U.S. Pat. No. 6,558,361 (Yeshurun) and U.S. Pat. No. 7,648,484 (Yeshurun et al.), which both describe hollow microneedle arrays and methods of manufacturing thereof.

Various embodiments of features of microneedles that can be employed in the microneedle articles of the present disclosure are described in PCT Publication No. WO 2012/074576 (Duan et al.), which describes liquid crystalline polymer (LCP) microneedles; and PCT Publication No. WO 2012/122162 (Zhang et al.), which describes a variety of different types and compositions of microneedles that can be employed in the microneedles of the present disclosure.

Articles comprising hollow microneedles having features according to the present disclosure can be made, for example, by injection molding processes that are known in the art. In some embodiments, the microneedle material can be (or include) a ceramic material, a metal, or a polymeric material, preferably a medical grade polymeric material. Exemplary types of medical grade polymeric materials include polycarbonate, liquid crystalline polymer (LCP), polyether ether ketone (PEEK), cyclic olefin copolymer (COC), polybutylene terephthalate (PBT). Preferred types of medical grade polymeric materials include polycarbonate and LCP.

The microneedle articles of the present disclosure can be manufactured in any suitable way such as by injection molding, compression molding, metal injection molding, stamping, or extrusion. In any embodiment, hollow microneedle arrays can be made by injection molding of a polymer such as medical grade polycarbonate or LCP, followed by laser drilling to form the channels of the hollow microneedles. Nonlimiting examples of molding processes for molding polymeric materials into solid microneedle articles can be found in U.S. Pat. No. 8,088,321 (Ferguson et al.) and U.S. Patent Application Publication Nos. 2012/0258284 (Rendon) and 2012/0041337 (Ferguson et al.), each of which is incorporated herein by reference in its entirety. A non-limiting example of a publication that discloses the formation of hollow channels in articles comprising microneedles is PCT Publication No. WO2014/105458, which is incorporated herein by reference in its entirety.

In some embodiments, the microneedle material can be (or include) a biodegradable polymeric material, preferably a medical grade biodegradable polymeric material. Exemplary types of medical grade biodegradable materials include polylactic acid (PLA), polyglycolic acid (PGA), PGA and PLA copolymer, polyester-amide polymer (PEA).

In some embodiments, the hollow microneedles can be a prepared from a dissolvable, degradable, or disintegradable material referred to herein as "dissolvable microneedles". A dissolvable, degradable, or disintegradable material is any solid material that dissolves, degrades, or disintegrates during use. In particular, a "dissolvable microneedle" dissolves, degrades, or disintegrates sufficiently in the tissue underlying the stratum corneum to allow a therapeutic agent to be released into the tissue. The therapeutic agent may be coated on or incorporated into a dissolvable microneedle. In some embodiments, the dissolvable material is selected from a carbohydrate or a sugar. In some embodiments, the dissolvable material is polyvinyl pyrrolidone (PVP). In some embodiments, the dissolvable material is selected from the group consisting of hyaluronic acid, carboxymethylcellulose, hydroxypropylmethylcellulose, methylcellulose, polyvinyl alcohol, sucrose, glucose, dextran, trehalose, maltodextrin, and a combination thereof.

In any embodiment, the hollow microneedles can be made from (or include) a combination of two or more of any of the above mentioned materials. For example, the tip of a microneedle may be a dissolvable material, while the remainder of the microneedle is a medical grade polymeric material.

A microneedle or the plurality of hollow microneedles in a microneedle-containing article of the present disclosure can have a variety of shapes that are capable of piercing the stratum corneum. In some of the embodiments, one or more of the plurality of microneedles can have a segment (e.g., a base segment, a tip segment, or a combination thereof) having a square pyramidal shape, triangular pyramidal shape, stepped pyramidal shape, conical shape, or the shape of a hypodermic needle. In any embodiment, a segment (e.g., a base segment, a tip segment, or a combination thereof) of one or more of the plurality of microneedles can have a square pyramidal shape. In any embodiment, a segment (e.g., a base segment, a tip segment, or a combination thereof) of one or more of the plurality of microneedles can have a triangular pyramidal shape. In any embodiment, a segment (e.g., a base segment, a tip segment, or a combination thereof) of one or more of the plurality of microneedles can have a stepped pyramidal shape. In any embodiment, a segment (e.g., a base segment, a tip segment, or a combination thereof) of one or more of the plurality of microneedles can have a conical shape. In any embodiment, a segment (e.g., a base segment, a tip segment, or a combination thereof) of one or more of the plurality of microneedles can have the shape of a hypodermic needle. In any embodiment, a microneedle array article may comprise an array of microneedles having a combination of any two or more of the foregoing microneedle shapes. The shape of any microneedle in the microneedle array article can be symmetric or asymmetric. The shape of any microneedle in the microneedle array article can be truncated (for example, the plurality of microneedles can have a truncated pyramid shape or truncated cone shape). In a preferred embodiment, each microneedle of the plurality of microneedles in a microneedle array article has a square pyramidal shape.

In any embodiment, each microneedle of the plurality of microneedles in a microneedle array article is a hollow microneedle (that is, the microneedle contains a hollow bore through the microneedle). The hollow bore can be from the base of the microneedle to the tip of the microneedle or the bore can be from the base of the microneedle to a position offset from the tip of the microneedle. In any embodiment, one or more of the plurality of hollow microneedles in a hollow microneedle array can have a segment having a conical shape, a cylindrical shape, a square pyramidal shape, a triangular pyramidal shape, or the shape of a hypodermic needle.

In any embodiment, one or more microneedle of the plurality of hollow microneedles in a hollow microneedle array article can have a conical shape; optionally, with a radius of curvature. In any embodiment, one or more microneedle of the plurality of hollow microneedles in a hollow microneedle array article can have a cylindrical shape. In any embodiment, one or more microneedle of the plurality of hollow microneedles in a hollow microneedle array article can have a segment (e.g., a base segment, a tip segment, or a combination thereof) having a square pyramidal shape. In any embodiment, one or more microneedle of the plurality of hollow microneedles in a hollow microneedle array article can have a segment (e.g., a base segment, a tip segment, or a combination thereof) having a triangular pyramidal shape. In any embodiment, one or more microneedle of the plurality of hollow microneedles in a hollow microneedle array article can have a segment (e.g., a base segment, a tip segment, or a combination thereof) having the shape of a hypodermic needle. In a preferred embodiment, each microneedle of the plurality of hollow microneedles in a hollow microneedle array article has a segment (e.g., a base segment, a tip segment, or a combination thereof) with the shape of a conventional hypodermic needle.

In any embodiment, an article comprising a hollow microneedle according to the present disclosure may comprise a plurality of the microneedles. The plurality of the microneedles optionally may form an array. In any embodiment, the article can comprise an array of about 3 to about 30, inclusive, of the hollow microneedles of the present disclosure. In a preferred embodiment, the article can comprise an array of about 8 to about 20, inclusive, of the hollow microneedles of the present disclosure. In a more-preferred embodiment, the article can comprise an array of 12, 16, or 18 of the hollow microneedles of the present disclosure.

In any embodiment of an article comprising a plurality of hollow microneedles according to the present disclosure, the overall height of each microneedle is about 400 µm to about 3000 µm. In any embodiment of an article comprising a plurality of hollow microneedles according to the present disclosure, the overall height of each microneedle is about 400 µm to about 2000 µm. In any embodiment of an article comprising a plurality of hollow microneedles according to the present disclosure, the overall height of each microneedle is about 750 µm to about 1600 µm.

In any embodiment of an article comprising a plurality of hollow microneedles according to the present disclosure, a hollow channel extending through each of the microneedles has a diameter, proximate the tip of the microneedle, of about 10 µm to about 200 µm. In any embodiment of an article comprising a plurality of hollow microneedles according to the present disclosure, a hollow channel extending through each of the microneedles has a diameter, proximate the tip of the microneedle, of about 10 µm to about 120 µm. In any embodiment of an article comprising a plurality of hollow microneedles according to the present disclosure, a hollow channel extending through each of the microneedles has a diameter, proximate the tip of the microneedle, of about 25 µm to about 75 µm.

In any embodiment of an article comprising a plurality of hollow microneedles according to the present disclosure, a hollow channel extending through each of the microneedles has a cross-sectional area of about 75 $\mu m^2$ to about 32,000 $\mu m^2$. In any embodiment of an article comprising a plurality of hollow microneedles according to the present disclosure, a hollow channel extending through each of the microneedles has a cross-sectional area of about 75 $\mu m^2$ to about 18,000 $\mu m^2$. In any embodiment of an article comprising a plurality of hollow microneedles according to the present disclosure, a hollow channel extending through each of the microneedles has a cross-sectional area of about 700 $\mu m^2$ to about 3,000 $\mu m^2$.

The hollow microneedle array articles of the present disclosure can be manufactured by injection molding of a polymer such as medical grade polycarbonate or LCP. Typically, these processes use molds to form the substrate with the microneedles extending therefrom.

In any embodiment, each hollow microneedle in an article according to the present disclosure can have a tip segment that has any shape or structure that facilitates, or does not interfere with, the ability of the microneedle to penetrate the surface of skin. In addition, the tip segment may comprise an opening (e.g., either a depression, dead-end cavity, or a through-hole that extends all the way through the microneedle) that facilitates the delivery of (and, optionally, storage therein) an active compound. In any embodiment, at least one hollow microneedle of the present disclosure comprises a base, an elongated body having a central axis and a body diameter, and a tip segment with two bevel faces. The tip segment comprises a tip, a first bevel face oriented diagonally with respect to the central axis and extending through about 75% to about 95% of the body diameter, a second bevel face oriented substantially perpendicular to the central axis and intersecting the first bevel face, a bevel opening defined by a first edge of the first bevel face and a second edge of the second bevel face. A microneedle tip with the aforementioned two bevel faces is described in PCT Publication No. WO2015/009524 and incorporated herein by reference in its entirety.

In any embodiment, at least one microneedle in an article according to the present disclosure can have a tip segment that comprises an opening that is formed by two channels that merge to form the opening. Thus, in these embodiments, the microneedle comprises a base, an elongated body having a central axis, a tip segment with a beveled surface and a bevel opening in the bevel surface, a first channel that extends axially from the bevel opening through at least a portion of the elongated body, and a second channel that extends radially from the first channel to the bevel opening. The first channel has a first wall that is substantially aligned with the central axis. The second channel has a second wall that is oriented substantially orthogonal to the central axis. The first channel and second channel merge to form the bevel opening. A microneedle tip that comprises an opening that is formed by two channels that merge to form the opening, is described in PCT Publication No. WO2015/009523 and incorporated herein by reference in its entirety.

In any embodiment, articles of the present disclosure can be used with an applicator (e.g., a single-use applicator or a reusable applicator) that is configured to urge the at least one microneedle of the article against a skin surface. In any embodiment, actuation of the applicator can occur through single actuation or through dual actuation. A non-limiting example of a single-actuation applicator is disclosed in US Patent Application Publication No. 2012/0123387 (Gonzalez et al.), which is incorporated herein by reference in its entirety. The use of microneedle articles with a dual-actuation or dual automatic actuation is described, for example, in PCT Publication No. WO2014/099404, which is incorporated herein by reference in its entirety.

In any embodiment, an article of the present disclosure can be used with an applicator comprising an adhesive assembly such as, for example, the applicator comprising the adhesive assembly described in PCT Publication No. WO2014/099404. In any embodiment, the adhesive assembly can comprise a skin-contact adhesive layer such as, for example, the applicator comprising the skin-contact adhesive layer described in PCT Publication No. WO2014/099404. In any embodiment, the skin-contact adhesive layer can comprise an annular configuration that, in use, surrounds the microneedle article of the present disclosure and, optionally, secures the article to a skin surface while an active compound (e.g., an active compound that is part of a pharmaceutical composition) is delivered from (or through) the hollow microneedle into a patient.

Figure 10:
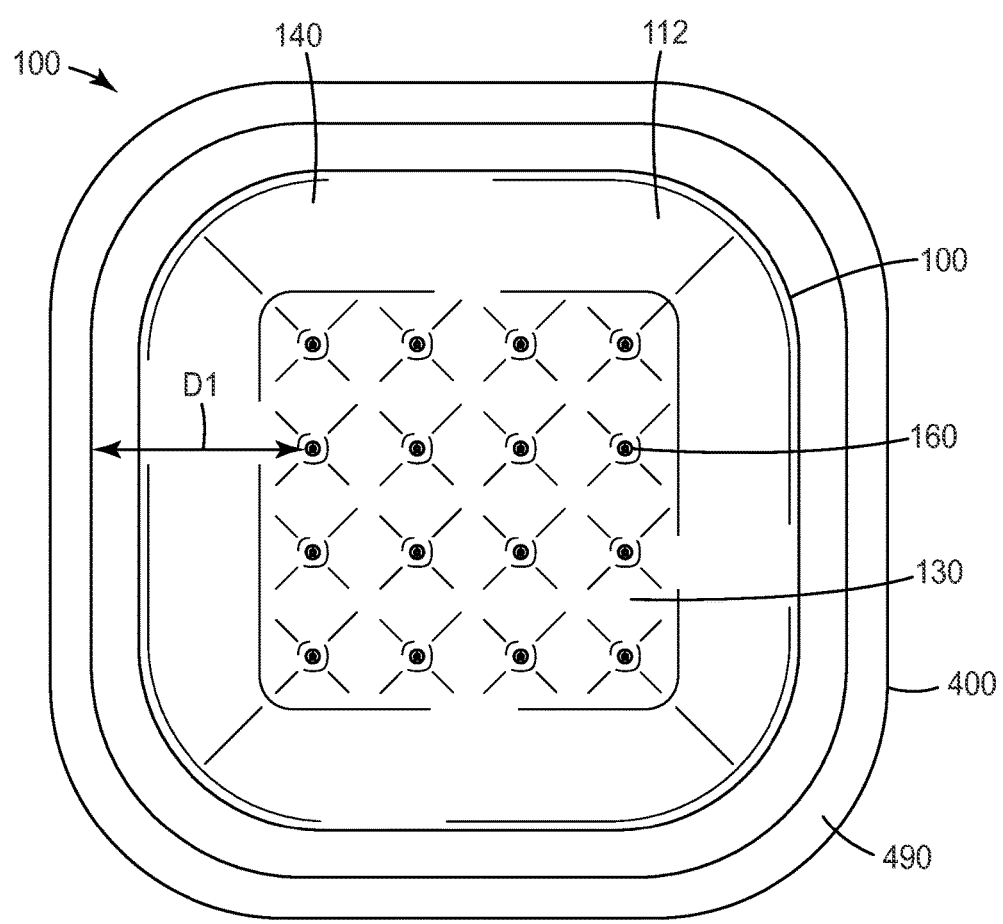
FIG. 10 is a plan view of an applicator coupled to an article comprising a plurality of microneedles according to the present disclosure; showing a distance between a perimeter microneedle of the article and an adhesive layer of the applicator.

FIG. 10 shows a plan view of a portion of the skin-facing surface of one embodiment of an applicator configured for use with an article comprising at least one microneedle according to the present disclosure. The applicator 400 comprises a skin-contact adhesive layer 490 that substantially surrounds the article 100. The article comprises a first side 112 that comprises a central portion 130 and a peripheral portion 140 that is not coplanar with the central portion 130 (i.e., the central portion 130 is projected from and, thus, on a different plane than the peripheral portion 140). A plurality of spaced-apart hollow microneedles 160 form an array that extends from the first side of the central portion 130. The article 100 is attached (e.g., detachably attached) to the applicator 400 using one of various attachment means (e.g., an adhesive, a clamp, friction fit, and the like, not shown) known in the art.

Also shown in FIG. 10 is spatial dimension D1 that is associated with the article 100 and the applicator. D1 is the distance between the tips of the perimeter microneedles and the skin-contact adhesive layer 490. In the illustrated embodiment, the central portion 130 is generally square-shaped and has a plurality of uniformly-distributed microneedles 160 that form a square-shaped array. The square-shaped array of the illustrated embodiment comprises twelve perimeter microneedles 160a and four interior microneedles 160b. In a preferred embodiment, the skin-contact adhesive layer is shaped and dimensioned so that the shortest distance between each microneedle tip in the array and the adhesive layer 490 is approximately equal (e.g., less than about 10% variability).

EXEMPLARY EMBODIMENTS

Embodiment A is an article, comprising:
a first side comprising:
  a central portion defined by a first edge;
  a microneedle-free peripheral portion that substantially surrounds the central portion; and
  a plurality of spaced-apart hollow microneedles extending from the central portion in a first direction;
wherein each microneedle of the plurality comprises a body that includes:
  an outer surface;
  a base segment having a base and a first shape that is defined by the outer surface;
  a tip segment having a tip and a second shape that is defined by the outer surface, wherein the second shape is distinct from the first shape;
  a transition plane that delineates the base segment and the tip segment;
  a hollow channel extending through the body of the microneedle from a first opening proximate the tip to a second opening proximate the base;
  a central axis;
wherein the plurality of hollow microneedles forms an array that comprises three or more perimeter microneedles disposed proximate the first edge;
wherein the central portion is not coplanar with the peripheral portion;
wherein the peripheral portion is canted in a second direction relative to the central portion, wherein the second direction is opposite the first direction;
wherein an angle, defined by an intersection of the central axis of at least one of the plurality of microneedles and a shortest line extending from the first edge and through the transition plane of the at least one microneedle, is less than about 50°.

Embodiment B is the article of Embodiment A, wherein the first angle is less than about 45°.

Embodiment C is an article, comprising:
a first side, comprising:
  a central portion defined by a first edge;
  a microneedle-free peripheral portion that substantially surrounds the central portion; and
  a plurality of spaced-apart hollow microneedles extending from the central portion in a first direction;
wherein each microneedle of the plurality comprises a body that includes:
  an outer surface;
  a base segment having a base and a first shape that is defined by the outer surface;
  a tip segment having a tip and a second shape that is defined by the outer surface, wherein the second shape is distinct from the first shape;
  a transition plane that delineates the base segment and the tip segment;
  a hollow channel extending through the body of the microneedle from a first opening proximate the tip to a second opening proximate the base;
  a central axis;

wherein the plurality of hollow microneedles forms an array that comprises three or more perimeter microneedles disposed proximate the first edge;

wherein the central portion is not coplanar with the peripheral portion;

wherein the peripheral portion is canted in a second direction relative to the central portion, wherein the second direction is opposite the first direction;

wherein each of the three or more perimeter microneedles comprises a height measured from the base to the tip;

wherein the tip segment of each of the three or more perimeter microneedles defines at least about 30% of the height of the at least one microneedle.

Embodiment D is the article of any one of Embodiments A through C, wherein each microneedle of the plurality comprises a microneedle height measured from the base to the tip, wherein the microneedle height of each microneedle of the plurality is about 600 microns to about 2000 microns.

Embodiment E is the article of Embodiment D, wherein each microneedle of the plurality comprises a first height component measured along the central axis from the base to the transition plane, wherein the first height component is about 500 µm to about 800 µm.

Embodiment F is the article of any one of the preceding Embodiments, wherein the perimeter microneedles define a two-dimensional first geometric shape, wherein the first geometric shape defines a first area, wherein the plurality of microneedles further comprises one or more interior microneedles that is substantially uniformly distributed within the first area.

Embodiment G is the article of any one of the preceding Embodiments, wherein the central portion comprises a microneedle tip-free second area within the first area, wherein the second area is at least about 15% of the first area.

Embodiment H is the article of Embodiment G, wherein the second area is up to about 99%, inclusive, of the first area.

Embodiment I is the article of any one of the preceding Embodiments, wherein the first geometric shape defines a substantially regular polygon.

Embodiment J is the article of any one of the preceding Embodiments, wherein the first edge defines a second geometric that is larger than, but substantially identical to, the first geometric shape.

Embodiment K is the article of Embodiment J, wherein the first edge comprises a plurality of corners, wherein at least one of the corners is curvate.

Embodiment L is the article of Embodiment K, wherein the at least one corner comprises a radius of curvature, wherein the radius of curvature is configured to maintain a constant distance between the first edge and the transition plane of a microneedle closest the at least one corner.

Embodiment M is the article of any one of the preceding Embodiments, wherein the peripheral portion is canted about 18 degrees to about 80 degrees in relationship to the central portion.

Embodiment N is the article of any one of the preceding Embodiments, wherein each of the perimeter microneedles has a shortest distance from its central axis and the first edge, wherein the shortest distance of all of the perimeter microneedles is approximately equal.

Embodiment O is the article of any one of the preceding Embodiments, wherein the central axis of each of the microneedles defines a longitudinal axis of the microneedle, wherein the outer surface of a base segment of each microneedle in the plurality of microneedles comprises a radius of curvature along the longitudinal axis.

Embodiment P is article of any one of the preceding Embodiments, wherein the article further comprises a side wall portion that extends from the peripheral portion, wherein the sidewall portion extends substantially in the second direction.

Embodiment Q is the article of any one of the preceding Embodiments, wherein the body of each microneedle of the plurality of microneedles comprises tip segment and a maximum diameter of the tip segment, wherein the tip segment of the at least one microneedle further comprises a bevel surface with a truncated bevel, wherein the truncated bevel is defined by a first plane extending diagonally from the tip toward the base through about 75% to about 95% of the body diameter and a second plane that intersects the first plane, wherein the second plane extends laterally from the outer surface through not more than 25% of the body diameter and is substantially perpendicular to the central axis, wherein the truncated bevel comprise a bevel opening that opens into a channel that extends into the body of the at least one microneedle.

Embodiment R is the article of any one of Embodiments A through P:

wherein the tip segment comprises a beveled surface and an opening in the beveled surface;

wherein at least one microneedle of the plurality of microneedles comprises a first channel that extends into the microneedle from the bevel opening along the central axis through at least a portion of the microneedle, and a second channel that extends radially from the first channel to the bevel opening;

wherein the first channel has a first wall that is substantially aligned with the central axis;

wherein the second channel has a wall that is oriented substantially orthogonal to the central axis;

wherein the first channel and second channel merge to form the bevel opening.

Embodiment S is the article of any one of the preceding claims, further comprising a reservoir that is in fluidic communication with the hollow channel.

Embodiment T is an assembly comprising an applicator with the article of any one of the preceding Embodiments operably attached thereto.

Embodiment U is the assembly of Embodiment T, wherein the applicator comprises an adhesive layer.

Embodiment V is the assembly of Embodiment U wherein a first distance between a first perimeter microneedle and the adhesive layer is approximately equal to a second distance between a second perimeter microneedle and the adhesive layer.

Embodiment W is the assembly of article V, wherein the first distance is about 90% to about 110% of the second distance.

Embodiment X is a use of the article of any one of Embodiments A through W, for injecting fluid into a body.

Embodiment Y is a use of the article of any one of Embodiments A through W, for extracting fluid from a body.

EXAMPLES

Example 1. Fabrication of Microneedle Articles

The microneedle array articles were prepared from polymeric material using standard injection molding procedures. The molded microneedle array articles were prepared using a mold assembly prepared from three mold sections with each section machined from steel. The first mold section contained projections that defined the beveled shape of the needle tip in the molded article. Each projection in the first mold section had a further cylindrical extension that defined features of the tip segment of the microneedles tip, including the opening on a bevel proximate the tip of the microneedle and a portion of the hollow channel extending through the body of each microneedle. The second mold section served as a template to define the pattern of the microneedles in the molded article, the external shape and size of the microneedles in the molded article, and the first major surface of the molded article (including the peripheral portion). The third mold section contained cylindrical projections emerging from a planar surface with each projection defining a portion of the microneedle hollow channel and the opening located at the base of each microneedle in the molded article. The planar surface from which the projections emerged served to define the second major surface of the base segment of the molded article. The first and second mold sections were assembled to form a tight fit by inserting the projections of the first mold section into the corresponding openings in the second mold section. The assembled first and second mold sections formed the first mold half. The third mold section was used as the second mold half.

The first and second mold halves were installed in a mold base in a 60-ton injection molding press (Sodick Plustech LA 60, Sodick Plustech Co., Yokohama, Japan). As is common in the art, the parting line of the mold assembly had both primary and secondary vents for general air evacuation during injection of the polymeric material. Vectra MT1300 liquid crystal polymer (LCP) pellets (Ticona Engineering Polymers, Florence, Ky.) were loaded into a reciprocating screw and heated until molten. The first mold half and second mold half were heated to a temperature (hereafter referred to as the "mold temperature at injection") of 200° F. (93.3° C.). The molding cycle was initiated by closing the first mold half with the second mold half. The molds were clamped together with approximately 20 to 60 tons of force. In the clamped position, the projections of the second mold half did not contact any surface of the first mold half. A first portion (approx. 50-95% of the part size volume) of the total amount of material from the reciprocating screw was injected into the mold chamber at a fixed velocity (hereafter referred to as the "injection velocity") of 7 inches/second (17.8 cm/second). After injecting the first portion of material, the process was switched from an injection-driven to a pressure-driven mode by applying a fixed pressure (hereafter referred to as the "pack pressure") of 13,500 psi (93,079 kilopascal) to force the remainder of the molten material into the negative mold insert. The pack pressure was applied for a fixed time (hereafter referred to as the "hold time") of 5 seconds. The pack pressure was subsequently released and the mold chamber was cooled to an ejection temperature set below the softening temperature of LCP. The mold chamber was opened and the microneedle array article was ejected.

Example 2. Injection Apparatus Used to Test the Microneedle Articles

Fully assembled microneedle article injection apparatuses similar to apparatuses described in U.S. Patent Application Publication No. US2012/0123387 (FIGS. 1-13) and PCT Publication No. WO2014/099404 (FIGS. 2, 14 and 15) were used. The drug cartridge in each apparatus contained a 1 mL solution of 0.005% methylene blue in five percent aqueous dextrose. The injection apparatus from Example 2 of PCT Publication No. WO2014/099404 was used with the following exceptions. First, the section of the apparatus joined to the adhesive assembly was not milled to remove material. Second, the construction of the adhesive assembly was different. Instead of using the four layer adhesive of PCT Publication No. WO2014/099404, the adhesive assembly used was a laminate composed of only two layers. The first layer was a 0.10 mm thick sheet of 3M 1510 double sided tape (available from the 3M Company). The second layer was a 0.07 mm sheet of 3M 1524 transfer adhesive. The two layer adhesive assembly was positioned to cover the first major surface of base member of the lower housing at the rounded end section of the device. The adhesive assembly laminate was laser cut so that the size and shape of the adhesive assembly was matched to that of the device. The two layers of the adhesive assembly each contained cut-out regions that were aligned to each other and exactly matched the opening in the device housing. The device and adhesive assembly were oriented so that the first layer of the adhesive assembly was adhered to the lower housing of the device. The adhesive assembly was aligned with the device so that the opening in the first layer of the adhesive assembly was coincident with the opening in the device. A release liner was used during storage of the device to protect the exposed adhesive of the fourth layer of the adhesive assembly.

The hollow microneedle array article (as shown in FIG. 1) used in the injection apparatus was injection molded (as described in Example 1) from Vectra MT1300 liquid crystal polymer (LCP) in the shape of a square approximately 1.6 $cm^2$ in area. The article featured 12 hollow microneedles centered on the article and arranged along the perimeter of a square pattern. The microneedles extended from the first major surface of the article. The microneedles were evenly spaced with 4 microneedles defining each side of the square. The peripheral portion surrounding the square microneedle pattern canted away from the perimeter of the pattern with an 18 degree slope (angle α in FIG. 4A). The spacing between neighboring microneedles was about 2 mm (as measured from tip to tip). The microneedles were oriented so that the openings in the tip segments were all aligned and facing toward one side of the square pattern. The external diameter of each microneedle at the base was about 2 mm. The flared base segment of each microneedle had a radius of curvature of about 0.7 mm. Each microneedle was in the shape of a triple bevel hypodermic needle (33.6 degree bevel with a split bevel of 20 degrees). The tip segment of each microneedle was shaped as shown in FIG. 3A. Each microneedle had a total height of about 1500 microns. The length of each tip segment (Note: the tip segment length, shown as height $H_{2B}$ in FIG. 3A, is measured from the tip to the transition plane that delineated the flared base segment from the substantially cylindrical tip segment) was about 635 microns with the external diameter at the midpoint of this region being about 254 microns (i.e. at a distance about 317.5 microns below the microneedle tip the external diameter of each microneedle was about 254 microns). The distance from the tip of each microneedle to the center of the opening near the tip was about 400 microns. The average diameter of the hollow channel created by molding in the tip segment was about 100 microns. In order to complete the hollow channel in each microneedle a section of material (about 50 microns) was removed using a laser drilling procedure (femtosecond) described in U.S. Provisional Patent Application No. 61/746,198. The diameter of the hollow channel of each microneedle in the laser drilled region was about 70 microns. The angle ($\theta_1$) was about 49.8 degrees (as shown in FIG. 6).

Example 3. Alternative Injection Apparatus

The same microneedle injection apparatus as described in Example 2 was used with the exception that the wire diameter of the U-shaped leaf-like insertion spring (i.e. first stored energy device as described in U.S. Patent Application Publication No. US2012/0123387 (FIGS. 1-13) and PCT Publication No. WO2014/099404 (FIGS. 2, 14 and 15) was 1.40 mm instead of 1.50 mm.

Example 4. Alternative Injection Apparatus

The same microneedle injection apparatus as described in Example 2 was constructed with the exception that a different hollow microneedle array article was used. The hollow microneedle article was injection molded (as described in Example 1) from Vectra MT1300 liquid crystal polymer (LCP) in the shape of a square approximately 1.6 cm$^2$ in area. The microneedles extended from the first major surface of the article. The article featured 16 hollow microneedles evenly spaced and defining a 4 by 4 square pattern centered on the article. The peripheral portion surrounding the square microneedle pattern was canted away from the perimeter of the central portion with an 18 degree slope relative to a plane formed by the central portion. The angle ($\alpha$) of the cant is shown in FIG. 4A. The spacing between neighboring microneedles was about 2 mm (as measured from tip to tip). The microneedles were oriented so that the openings in the tip segments were all aligned and facing toward one side of the square pattern. The external diameter of each microneedle at the base was about 2 mm. The flared base segment of each microneedle had a radius of curvature of about 0.7 mm. Each microneedle was in the shape of a triple bevel hypodermic needle (33.6 degree bevel with a split bevel of 20 degrees). The tip segment of each microneedle was shaped as shown in FIG. 3A. Each microneedle had a total height of about 1500 microns. The length of each tip segment (Note: the tip segment length, shown as height $H_{2B}$ in FIG. 3A, is measured from the tip to the transition plane that delineated the flared base segment from the substantially cylindrical tip segment) was about 635 microns with the external diameter at the midpoint of this region being about 254 microns (i.e. at a distance about 317 microns below the microneedle tip the external diameter of each microneedle was about 254 microns). The distance from the tip of each microneedle to the center of the opening near the tip was about 400 microns. The average diameter of the hollow channel created by molding in the tip segment was about 100 microns. In order to complete the hollow channel in each microneedle a section of material (about 50 microns) was removed using a laser drilling procedure (femtosecond) described in U.S. Provisional Patent Application No. 61/746,198. The diameter of the hollow channel of each microneedle in the laser drilled region was about 70 microns. The angle ($\theta_1$) was about 49.8 degrees (as shown in FIG. 6).

Example 5. Use of Microneedle Article to Inject a Substance

The study was conducted using Yorkshire cross domestic pigs (Midwest Research Swine, Gibbon, Minn.) in vivo. A soft region of the belly having minimal muscle content was selected as the application site for microneedle insertion. The application site was first trimmed with an electric clipper and then shaved using a razor and shaving cream. The shaved area was scrubbed using soapy water and a BUF-PUF exfoliation sponge (3M Company, St. Paul, Minn.) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus of Example 3 was used. The release liner was removed from the adhesive assembly and the apparatus was adhered to the skin of the pig. During attachment of the device to the pig, the skin at the application site was gently stretched to provide a slight tension to the skin. The skin was then allowed to relax and the push-button was depressed to cause release of the applicator element and insertion of the microneedle array article into the skin of the pig. Removal of the tapered pin from the housing released the coiled spring which initiated the injection of the methylene blue solution into the pig. After completion of the injection, the apparatus was maintained on the skin for one additional minute. The apparatus was removed from the skin and the skin surface was examined to determine if there was any methylene blue solution on the surface of the skin. The presence of methylene blue solution on the skin was an indication that not all of the methylene blue was injected into the animal. The injection site was wiped with a pre-tared absorbent wipe and the wipe was then weighed to determine the amount of methylene blue that was not successfully delivered.

A total of three replicates were conducted. The injection times ranged from 54 to 73 seconds with the average injection time being 62 seconds. One of the apparatuses successfully delivered the methylene blue solution without any "leakage" (i.e. no methylene blue solution was observed on the skin surface). The other two apparatuses successfully delivered 91% and 98% of the methylene blue solution, respectively.

Example 6. Use of Microneedle Article

A study was conducted to determine the depth of penetration (DOP) of the microneedles of the array when applied to the skin surface of a Yorkshire cross domestic pigs (Midwest Research Swine), in vivo. The hollow microneedle array article described in Example 4 was used.

The microneedles on the article were coated using a three step process. The first two steps involved applying primer coatings to the microneedles and the third step involved applying a thin coating of Rhodamine B to the microneedles. In Step 1, the array articles were flood coated with a 35 microliter solution containing 0.5 mg/mL polyvinyl alcohol (80% hydrolyzed) (Sigma-Aldrich, Inc., St. Louis, Mo.) and 35 µg/ml of TWEEN® 80 (Sigma-Aldrich) in 90% (w/v) ethanol. The coated articles were then dried at 35° C. for 20 µmutes. In Step 2, the articles from Step 1 were flood coated with 35 microliters of an aqueous solution of 33.3 mg/ml aluminum potassium sulfate (Penta Manufacturing, Livingston, N.J.). The coated articles were then dried at 35° C. for 30 µmutes. In Step 3, the primed articles from Step 2 were flood coated with 40 microliters of an aqueous solution of 0.08% (w/v) Rhodamine B (Sigma-Aldrich). The coated articles were dried at 35° C. for 30 µmutes. The three step process provided articles in which the microneedles were completely covered with a thin, opaque coating of Rhodamine B.

The ham region was selected as the application site for microneedle insertion. The application site was first trimmed with an electric clipper and then shaved using a razor and shaving cream. The shaved area was scrubbed using soapy water and a BUF-PUF exfoliation sponge (3M Company) and then rinsed with deionized water. The animal was placed in a lateral recumbent position on a heated table (38° C.). The animal was anesthetized with isofluorene gas and maintained under anesthesia throughout the experiment. The application site was then wiped with a 70% isopropanol in water solution.

The injection apparatus described in Example 4 with a Rhodamine B coated article was applied to the pig skin. The push-button was depressed to cause release the applicator element and insertion of the microneedles of the microneedle array into the skin of the pig. The applicator was maintained on the skin for an additional 5 μmutes.

The applicator was removed from the animal. The depth of penetration (DOP) of the microneedles into the pig skin was determined indirectly by measuring the distance from the tip of the microneedle to where the Rhodamine B coating was wiped or dissolved from the microneedle after application into the skin. The measurement was conducted using a Nikon LV-100 microscope at 100× magnification (Nikon Instruments, Melville, N.Y.) with Image Pro® Plus digital image analysis software (Media Cybernetics, Bethesda, Md.). A total of two replicates were conducted. The mean microneedle DOP was determined by sampling all of the microneedles from each article (n=32). The results are presented in Table 1.

| | |
|---|---|
| Minimum DOP | 386 microns |
| Maximum DOP | 835 microns |
| Mean DOP (n = 32) | 595 microns |
| Standard Deviation | 119 microns |
| % RSD | 20% |

Example 7. Use of Microneedle Article

The procedure as described in Example 6 was used with the exception that the apparatus of Example 2 was used instead of the apparatus of Example 4. The results are presented in Table 2.

TABLE 2

Depth of Penetration DOP of Microneedles when Microneedle Article was Applied to the Ham Area (Example 7).

| | |
|---|---|
| Minimum DOP | 315 microns |
| Maximum DOP | 934 microns |
| Mean DOP (n = 24) | 736 microns |
| Standard Deviation | 125 microns |
| % RSD | 17% |

Example 8. Use of Microneedle Article to Inject a Substance

A study was conducted in human subjects (17 male, 23 female) to determine the time required to inject 1 mL of a 5% dextrose USP injection solution. The apparatus and hollow microneedle array article described in Example 2 was used with the exception that the drug cartridge was filled with the 5% dextrose USP injection solution instead of the methylene blue solution. The release liner was removed from the adhesive assembly and the apparatus was adhered to the thigh region of the subject. The push button was depressed to insert the microneedles into the skin of the subject. Next, the tapered pin was removed from the housing to release the coiled spring and begin the injection of the dextrose solution into the subject. The timer was started at the time of pin removal and stopped when the plunger was observed to reach the end of travel in the cartridge. The apparatus was removed from the subject and the skin surface around the application site was swabbed with a dry swab. The mass of the swab was measured immediately before and immediately after swabbing. The amount of residual fluid on the skin surface was determined by calculating the difference in the swab measurements. No attempt was made to differentiate between the different types of fluid (such as blood, interstitial fluid, or dextrose solution) found on the skin surface. The results are presented in Tables 3 and 4.

TABLE 3

Injection Time

| | Male Subjects | Female Subjects |
|---|---|---|
| Minimum Injection Time (sec) | 27 | 17 |
| Maximum Injection Time (sec) | 332 | 228 |
| Mean Injection Time (sec) | 110 | 67 |
| Standard Deviation (sec) | 86 | 57 |

TABLE 4

Fluid Recovery

| | Male Subjects | Female Subjects |
|---|---|---|
| Minimum Amount of Fluid at Site | 0 mg | 0 mg |
| Maximum Amount of Fluid at Site | 4 mg | 20 mg |
| Mean Amount of Fluid at Site | 2 mg | 2 mg |
| Standard Deviation | 3 mg | 4 mg |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:
1. An article, comprising:
  a first side comprising:
    a central portion defined by a first edge;
    a microneedle-free peripheral portion that substantially surrounds the central portion; and
    a plurality of spaced-apart hollow microneedles extending from the central portion in a first direction;
  wherein each microneedle of the plurality comprises a body that includes:
    an outer surface;
    a base segment having a base and a first shape that is defined by the outer surface;

a tip segment having a tip and a second shape that is defined by the outer surface, wherein the second shape is distinct from the first shape;
a transition plane that delineates the base segment and the tip segment;
a hollow channel extending through the body of the microneedle from a first opening proximate the tip to a second opening proximate the base;
a central axis;
wherein the plurality of hollow microneedles forms an array that comprises three or more perimeter microneedles disposed proximate the first edge;
wherein the central portion is not coplanar with the peripheral portion;
wherein the peripheral portion is canted in a second direction relative to the central portion at an angle of 10° to 80°, wherein the second direction is opposite the first direction;
wherein an angle, defined by an intersection of the central axis of at least one of the plurality of microneedles and a shortest line extending from the first edge and through the transition plane of the at least one microneedle, is less than about 50°.

2. The article of claim 1, wherein the first angle is less than about 45°.

3. The article of claim 1, wherein each microneedle of the plurality comprises a microneedle height measured from the base to the tip, wherein the microneedle height of each microneedle of the plurality is about 600 microns to about 2000 microns.

4. The article of claim 3, wherein each microneedle of the plurality comprises a first height component measured along the central axis from the base to the transition plane, wherein the first height component is about 500 m to about 800 m.

5. The article of claim 1, wherein the perimeter microneedles define a two-dimensional first geometric shape, wherein the first geometric shape defines a first area, wherein the plurality of microneedles further comprises one or more interior microneedles that is substantially uniformly distributed within the first area.

6. The article of claim 1, wherein the central portion comprises a microneedle tip-free second area within the first area, wherein the second area is at least about 15% of the first area.

7. The article of claim 6, wherein the second area is up to about 99%, inclusive, of the first area.

8. The article of claim 1, wherein the first geometric shape defines a substantially regular polygon.

9. The article of claim 1, wherein the first edge defines a second geometric that is larger than, but substantially identical to, the first geometric shape.

10. The article of claim 9, wherein the first edge comprises a plurality of corners, wherein at least one of the corners is curvate.

11. The article of claim 1, wherein the peripheral portion is canted about 18 degrees to about 80 degrees, inclusive, in relationship to the central portion.

12. The article of claim 1, wherein each of the perimeter microneedles has a shortest distance from its central axis and the first edge, wherein the shortest distance of all of the perimeter microneedles is approximately equal.

13. The article of claim 1, wherein the central axis of each of the microneedles defines a longitudinal axis of the microneedle, wherein the outer surface of a base segment of each microneedle in the plurality of microneedles comprises a radius of curvature along the longitudinal axis.

14. The article of claim 1, wherein the article further comprises a side wall portion that extends from the peripheral portion, wherein the sidewall portion extends substantially in the second direction.

15. The article of claim 1, wherein the body of each microneedle of the plurality of microneedles comprises tip segment and a maximum diameter of the tip segment, wherein the tip segment of the at least one microneedle further comprises a bevel surface with a truncated bevel, wherein the truncated bevel is defined by a first plane extending diagonally from the tip toward the base through about 75% to about 95% of the body diameter and a second plane that intersects the first plane, wherein the second plane extends laterally from the outer surface through not more than 25% of the body diameter and is substantially perpendicular to the central axis, wherein the truncated bevel comprise a bevel opening that opens into a channel that extends into the body of the at least one microneedle.

16. The article of claim 1:
wherein the tip segment comprises a beveled surface and an opening in the beveled surface;
wherein at least one microneedle of the plurality of microneedles comprises a first channel that extends into the microneedle from the bevel opening along the central axis through at least a portion of the microneedle, and a second channel that extends radially from the first channel to the bevel opening;
wherein the first channel has a first wall that is substantially aligned with the central axis;
wherein the second channel has a wall that is oriented substantially orthogonal to the central axis;
wherein the first channel and second channel merge to form the bevel opening.

17. The article of claim 1, further comprising a reservoir that is in fluidic communication with the hollow channel.

18. A method of using the hollow microneedle article of claim 1, the method comprising injecting fluid from the hollow microneedle article into a body.

19. A method of extracting fluid from a body, the method comprising contacting the hollow microneedle article of claim 1 with fluid within a body and extracting the fluid from the body into one or more of the hollow microneedles of the hollow microneedle article.

* * * * *

UNITED STATES PATENT AND TRADEMARK OFFICE
CERTIFICATE OF CORRECTION

PATENT NO.         : 10,099,043 B2
APPLICATION NO.    : 14/905018
DATED              : October 16, 2018
INVENTOR(S)        : Dennis Berry et al.

It is certified that error appears in the above-identified patent and that said Letters Patent is hereby corrected as shown below:

In the Specification

Column 9
Line 36, Delete "Jims." and insert -- µm. --, therefor.

Column 22
Line 54, Delete "µmutes." and insert -- minutes. --, therefor.
Line 58, Delete "µmutes." and insert -- minutes. --, therefor.
Line 61, Delete "µmutes." and insert -- minutes. --, therefor.

Column 23
Line 14, Delete "µmutes." and insert -- minutes. --, therefor.

In the Claims

Column 25
Line 35 (Approx.), In Claim 4, delete "m" and insert -- µm --, therefor.
Line 35 (Approx.), In Claim 4, delete "m." and insert -- µm. --, therefor.

Signed and Sealed this
Fourteenth Day of May, 2019

Andrei Iancu
*Director of the United States Patent and Trademark Office*